United States Patent
Tiongson

[11] Patent Number: 6,077,535
[45] Date of Patent: Jun. 20, 2000

[54] DIRECT COMPRESSION CARBONYL IRON TABLET

[75] Inventor: Antonio Tiongson, Neshanic Station, N.J.

[73] Assignee: SmithKline Beecham Corporation, Philadelphia, Pa.

[21] Appl. No.: 09/091,386

[22] PCT Filed: Dec. 20, 1996

[86] PCT No.: PCT/US96/20344

§ 371 Date: Oct. 2, 1998

§ 102(e) Date: Oct. 2, 1998

[87] PCT Pub. No.: WO97/22336

PCT Pub. Date: Jun. 26, 1997

Related U.S. Application Data

[60] Provisional application No. 60/009,014, Dec. 21, 1995.

[51] Int. Cl.⁷ ........................................................ A61K 9/20
[52] U.S. Cl. ........................ 424/464; 424/465; 514/904; 514/905
[58] Field of Search ..................................... 424/464, 465; 514/904, 905

[56] References Cited

U.S. PATENT DOCUMENTS

| | | |
|---|---|---|
| 5,541,158 | 7/1996 | Vance et al. . |
| 5,851,553 | 12/1998 | Myers et al. ............................. 424/488 |
| 5,869,084 | 2/1999 | Paradissis et al. ...................... 424/439 |

FOREIGN PATENT DOCUMENTS 0 687 464  12/1995  European Pat. Off. .

OTHER PUBLICATIONS

Database WPI, Section Ch, Week 9344, Derwent Publication Ltd., London; GB; Class B05, AN 93–347355, XP002093170 & HU 208 085 B (Reanal Finomvegyszergyar), Aug. 30, 1993, see abstract.

Neumuller O.–A.: "Rompps Chemie–Lexikon" 1901, Franckh'Sche Verlagshandlung, Stuttgart, XP002093169, p. 946, p. 949.

*Primary Examiner*—Thurman K. Page
*Assistant Examiner*—Todd D Ware
*Attorney, Agent, or Firm*—Nora Stein-Fernandez; Janice E. Williams; Charles M. Kinzig

[57] ABSTRACT

This invention relates to a pharmaceutical composition for use as a direct compression tableting agent containing carbonyl iron and a process for making the same.

1 Claim, No Drawings

DIRECT COMPRESSION CARBONYL IRON TABLET

This application claims benefit of Provisional Application 60/009,014 filed Dec. 21, 1995.

FIELD OF THE INVENTION

This invention relates to a composition for use as a direct compression tableting agent for a tablet containing carbonyl iron and the process for making the same. More particularly, this invention relates to a pharmaceutical composition for a direct compression tableting agent comprising a pharmacologically active amount of carbonyl iron and sorbitol as a carrier. The instant compressible carbonyl iron composition overcomes the disadvantages associated with directly compressing carbonyl iron tablets. The inventive carbonyl iron tablet composition is useful for the treatment and/or prophylaxis of conditions wherein iron is indicated, for example, as a dietary supplement to alleviate anemia, or as a nutritional supplement.

BACKGROUND OF THE INVENTION

As a solid dosage form, the tablet is the most popular and useful form of oral medication for dispensing active ingredients such as pharmaceuticals, vitamins, and minerals. The compressed tablet offers several advantages over other solid dosage forms. These advantages include greater accuracy of dosage, more convenient administration, increased durability and stability during storage, shorter production time, and economy and efficiency in storage, packaging and shipping.

Tablets can be prepared using several established methods such as wet granulation, dry granulation, and direct compression. The most desirable method from the standpoint of the processing procedures, equipment and materials is the direct compression method. This method increases the efficiency of tableting operations and reduces costs by requiring the least amount of space and labor.

In a dry direct compression method, the ingredients are simply dry-mixed and then compressed. There is no granulation stage. It is essential that each component is uniformly dispersed within the mixture. Any tendency for component segregation must be minimized to assure that each tablet contains an accurate reproducible dosage. In addition, the mixture must have certain flow characteristics to allow accurate and convenient transport and must be cohesive when compressed. To reduce segregation tendencies the particle size distribution, shape, and density of all the ingredients should be similar. There are only a few substances available in forms which could be compressed directly without further treatment. If these ingredient characteristics are not present, then one of the granulation methods should probably be used.

There are some limitations to the use of direct compression tableting. First, while compression of some components may produce tablets that do not disintegrate, other components of the tablet may interfere with the compressibility of the tablet composition and thus minimize the usefulness of this method. Second, most materials possess relatively weak intermolecular attraction thereby affecting the compacting of the ingredients into tablets. Third, with some formulations, the percentage of active ingredient is so small that direct compression would be impractical and uneconomical. However, in this case, an inert compressible diluent can be used to increase bulk in order to make the tablet a practical size for compression.

The direct compression method is a rather simple procedure compared to the more complicated and time consuming wet process method. Relatively inexpensive and unreactive chemicals are commonly used as the major component in direct compressible formulations. However, only a very limited number of materials possess the necessary cohesive strength and flowability to allow direct compression without requiring granulation. Modification is often required either by treating the material in some manner during the earlier stages of preparation or by adding a binder or excipient material which will surround or coat the active ingredient thereby forming an easily compressible excipient. The limitations associated with the direct compression method are of particular concern when tableting an active ingredient such as carbonyl iron. Therefore, a composition and method for tableting carbonyl iron by the direct compression technique is an important development in the art.

SUMMARY OF THE INVENTION

The present invention is directed to a uniform, low dose, pharmaceutically acceptable carbonyl iron tablet composition formulated by the direct compression method. The process of tableting using the composition is also described. Carbonyl iron, a form of iron that is non-toxic and well tolerated even in large doses, is a highly purified elemental form of iron produced by the decomposition of iron pentacarbonyl as a dark gray powder. Carbonyl iron has a minimum 98% iron content. What distinguishes carbonyl iron is its fine spherical size of 2-microns which is an order of magnitude smaller than other commercial iron forms. Carbonyl iron is commercially available in pharmaceutical/food grade from ISP under the trade name FERRONYL® iron (hereinafter carbonyl iron).

One would expect that use of the direct compression method in tableting carbonyl iron would present many problems and limitations due to certain inherent properties of carbonyl iron. For example, since carbonyl iron has a high density it tends to fall to the bottom of a typical tablet mixture comprising carbonyl iron as a carrier and excipients, thereby creating a non-homogeneous mixture. In addition, carbonyl iron has poor compressibility characteristics, therefore, it does not have a propensity to form a tablet when compacted. Further, due to its moisture sensitivity, carbonyl iron is susceptible to chemical degradation or alteration (e.g., oxidation) on exposure to moisture. This characteristic would discourage using a wet granulation method for tableting carbonyl iron containing products. Yet further, carbonyl iron has a tendency to adhere to the equipment used for tableting, which ultimately effects the uniformity of the mixture and the potency of the final formulation.

An additional factor to overcome in formulating carbonyl iron into a tablet using the direct compression method according to this invention was the fact that known direct compression diluents, for example, sorbitol, lactose, starch, microcrystalline cellulose, dicalcium phosphate and tricalcium phosphate have very different density profiles from carbonyl iron. This presented a problem with using the direct compression method since, typically, when two materials having very different density profiles are mixed together, one would not expect a uniform mixture to result since there will be segregation of the two materials, with the denser material falling out of the mixture.

However, despite the density difference between sorbitol and carbonyl iron (approximately 0.5 versus 4.2) the use of sorbitol as a carrier in the present inventive composition, unexpectedly enabled the formation of a uniformly blended carbonyl iron tablet made by the direct compression method. Without being bound to a particular theory, it is believed that the instant combination of carbonyl iron and sorbitol is successfully tabletted because of sorbitol's extremely high adsorption potential for carbonyl iron and its ability to retain adsorption without carbonyl iron segregating from the sorbitol carrier. This occurs despite the significant density differences between the sorbitol carrier and the active ingredient carbonyl iron. The tablet achieved by the instant invention is highly uniform, low dose and pharmaceutically acceptable, thereby overcoming the known limitations of tabletting carbonyl iron especially by the direct compression method.

DETAILED DESCRIPTION OF THE INVENTION

A new pharmaceutically acceptable direct compression tableting composition is described which allows the active ingredient, carbonyl iron, to be uniformly distributed within the tablet matrix. The carrier suitable for use in preparing the new direct compression tableting composition is also described.

Specifically, the inventive composition consists of carbonyl iron. In a preferred embodiment, carbonyl iron is suitably present in an amount of about 8.0–9.0 percent weight/weight ("% w/w") of the total composition. More preferably, carbonyl iron is present in an amount of about 8.3–8.6% w/w of the total composition.

The carrier used to produce the inventive composition comprises sorbitol. Sorbitol is a commercially available compound which is widely used in pharmaceutical compositions. A preferred grade of sorbitol for use in the present composition is KARION®, either food grade or pharmaceutical grade, available from E. Merck, Dermstadt. KARION® is a spray dried form of sorbitol. A granulated form of sorbitol, for example, NEOSORB®, available from Roquette Corp. may also be used in the instant composition. Sorbitol is suitably present in the instant composition in a range of about 40 to 46% w/w of the total composition. Preferably, sorbitol is present in a range of about 42 to 45% w/w of the total composition.

The instant carrier may also contain lactose (commercially available from Sheffield Products) as a water-soluble filler for the carrier. If lactose is used as a filler for the sorbitol carrier, it is suitably present in an amount of between about 40 to 45% w/w of the total composition, preferably between about 42 to about 45% w/w.

Other excipients, alone or in any suitable combination, which may optionally be used with the instant composition are as follows. Suitably, crospovidone may be used as a disintegrant. Further, a water-soluble lubricant such as polyethylene glycol may be present in the composition. Yet further, a water-insoluble lubricant such as magnesium stearate or stearic acid may also be used. In addition, various colorants, flavoring agents and/or sweetening agents may be used in the instant known composition. Also, as would be understood by the skilled artisan, the instant directly compressed tablet may be formulated as a chewable or a swallowable tablet. The carbonyl iron tablet may be formulated in any desired dosage form, but preferably a 50 mg dosage form is made.

Sorbitol was discovered to be the ideal carrier for a carbonyl iron tablet formulated by the direct compression technique based on experimental data obtained according to the following examples. Properties of various excipients significant to direct compression tabletting of carbonyl iron were tested which resulted in a determination that the sorbitols tested were the optimum carriers for use in the inventive composition.

TAP DENSITY/COMPRESSIBILITY STUDY

Tap and bulk densities, as well as compressibility ratios of all the excipients being tested and carbonyl iron were determined by a Vanderkamp Tap Density Tester at intervals of 50 taps for a total of 500 taps. The compressibility ratio is a measure of the compressibility of a material, i.e., calculated by the formula Tap Density minus Bulk Density divided by Tap Density.

The results of the Tap Density and Compressibility Ratio measurements can be found in Table 1. Since none of the excipients tested had a density comparable to carbonyl iron, uniformity problems in a dry blend process were anticipated. Therefore, another method of blending, for example, adsorption, was evaluated.

TABLE 1

| No. | Material | Tap Density | Compressibility Ratio |
|---|---|---|---|
| 1 | Karion ® | 0.464 | 0.212 |
| 2 | Karion FG ® | 0.467 | 0.200 |
| 3 | Neosorb ® | 0.711 | 0.126 |
| 4 | Lactose | 0.796 | 0.260 |
| 5 | Avicel ® | 0.399 | 0.302 |
| 6 | Emocel ® | 0.399 | 0.312 |
| 7 | NuTab ® | 0.818 | 0.149 |
| 8 | Starch 1500 | 0.797 | 0.210 |
| 9 | Starch 1500 LM | 0.879 | 0.293 |
| 10 | Ferronyl ® (carbonyl iron) | 4.190 | 0.280 |

ADSORPTION STUDY

Since none of the excipients had a density comparable to carbonyl iron, adsorption of carbonyl iron onto the excipients was evaluated. The study was conducted to determine the amount of carbonyl iron adsorbed onto each excipient using a Varian Atomic Adsorption Spectrometer which can detect elemental iron at levels as low as 1 ppm. The detailed procedure is as follows, with the results collected in Table 2.

Procedure: The general procedure followed is outlined below:

I. Preparation of samples:

1. 50 g of carbonyl iron and 150 g of excepient were mixed in a 500 mg capacity V-blender for 10 minutes.

2. The blend was then sieved through a set of standard sieves for 5 minutes at vibration level 2.

3. The fractions retained on each of the sieves 20, #40, #60, #100, #200, #325 and the bottom pan were collected and weighed.

4. The #40/60 fraction was used to determine the amount of carbonyl iron adsorbed in all excepients.

II. Analysis of Samples:

1. 200 mg of blend was weighed and digested with 20 ml of 10% HCl.

2. Appropriate dilutions were made to bring the concentration of carbonyl iron to about 5 ppm.

3. The samples were then analysed by Atomic Absorption Spectrometer against the respective standards. (Deionised water was used to zero the instrument).

4. The Atomic Absorption parameters using Fe lamp were:

wavelength—248.3 nm slit opening—0.2 mm lamp current—5 mA air pressure—60 psi
acetylene pressure—12 psi

TABLE 2

| No. | Ferronyl with | % Ferronyl adsorbed |
|---|---|---|
| 1 | Starch 1500 LM | 5.97 |
| 2 | Starch 1500 | 8.42 |
| 3 | Lactose N.F. | 9.61 |
| 4 | NuTab ® | 16.75 |
| 5 | Emcocel ® 50-M | 17.31 |
| 6 | Avicel ® PH-101 | 17.47 |
| 7 | Neosorb ® 30/60 | 32.66 |
| 8 | Karion ® FG | 33.57 |
| 9 | Karion ® | 42.31 |

Since the starches adsorbed the least amount of carbonyl iron, they were eliminated from further experimental analysis. However, since Neosorb® and the Karions®, i.e., the sorbitols, surprisingly adsorbed a large amount of carbonyl iron, they were subjected to further experimental analysis, in particular, examination of surface characteristics of the excipients.

Since the results of the adsorption studies indicated a 25% difference between the carbonyl iron adsorption capacity of Neosorb® and Karion®, a scanning electron microscopy (S.E.M.) study was performed in order to investigate how this difference might influence the direct compression tableting of carbonyl iron.

Procedure:

1. A small sample of each excipient blended with carbonyl iron was glued on a metal stud and then micro-plated with gold and platinum in sets of four.
2. The studs were then placed under the S.E.M. and their surface characters observed on a screen.
3. Polaroid snapshots of the surface characteristics were taken at magnifications which best showed the contrast.
4. Steps 2 and 3 were repeated for each of the samples.

Results:

The surface of Karion® shows hair-like projections which are far more numerous than those on Neosorb®. Without being bound to any theory, it appears that these hair-like projections might be responsible for the higher adsorption profiles of the Karion® sorbitols over the Neosorb® sorbitol.

MOISTURE CONTENT STUDY:

Low moisture content was considered to be a necessary property for the excipient to be blended with carbonyl iron in order to enhance the stability of the iron. Therefore, the moisture content of each potential excipient and of carbonyl iron was determined in order to find the excipient with the least inherent moisture. The moisture content was measured using a Computrac Max-50 moisture analyser at a pre-set temperature of 120° C. The results of this study can be found in Table 3.

Conclusions:

1. The Karions® and Neosorb® (sorbitols) and lactose each have a very low moisture content making them acceptable excipients for carbonyl iron.
2. The microcrystalline celluloses have just under 5% moisture content and would be acceptable as excipients for carbonyl iron if they do not pick-up any more moisture.
3. The starches are unacceptable as excipients for carbonyl iron because of their high moisture content.

Therefore, moisture pickup was determined for all potential excipients in order to gather data regarding how the excipients behave with respect to time. In addition, moisture pickup at different humidity levels was assessed in order to determine the optimum working humidity conditions. The goal was to prevent moisture pickup during tablet formulation.

TABLE 3

| No. | Sample Name | % Moisture |
|---|---|---|
| 1 | Karion ® | 0.35 |
| 2 | Karion ® FG | 0.32 |
| 3 | Neosorb ® | 0.32 |
| 4 | Avicel ® PH-101 | 4.47 |
| 5 | Emcocel ® 50-M | 4.28 |
| 6 | Lactose N.F. | 0.57 |
| 7 | NuTab ® | 0.90 |
| 8 | Starch 1500 | 10.70 |
| 9 | Starch 1500 LM | 5.54 |

MOISTURE PICKUP STUDY:

Procedure:

1. Humidity chambers were prepared with the relative humidities ("RH") at 25° C., as found in Table 4.
2. Approximately 1 gram of each excipient was weighed in sets of four and transferred immediately to the four humidity chambers.
3. The weight gain or loss in the pans was noted at the time intervals of 3 hrs., 6 hrs., 24 hrs., 48 hrs., 72 hrs., 96 hrs., and 168 hrs., (i.e., 7 days), making the duration of the study 7 days long.

TABLE 4

| No. | Composition of medium | % RH |
|---|---|---|
| 1 | saturated $CaCl_2.6H_2O$ solution | 31 |
| 2 | saturated $Na_2Cr_2O_2.2H_2O$ solution | 52 |
| 3 | saturated $NaNO_2$ solution | 66 |
| 4 | saturated $ZnSO_4.7H_2O$ solution | 90 |

Results:

1. Lactose picked up the least amount of moisture at 90% RH by day seven.
2. The sorbitol excipients picked up less than 3% moisture at up to 66% RH. But at 90% RH, th sorbitols picked up excessive amounts of moisture.
3. The microcrystalline cellulose excipients picked up less than 3% moisture at humidities of up to 66% RH and about 8% moisture at 90% RH.

Conclusions:

It was decided that up to 66% RH was an acceptable humidity level when working with sorbitol excipients and microcrystalline cellulose excipients.

FLOWABILITY STUDY:

The flow properties of each excipient were studied with and without the carbonyl iron adsorbed onto them. These measurements were used to determine a Flowability Index for each excipient, defined as the diameter of the smallest ring through which the powder flows three times out of three, as determined by the Flowdex Tester Model 211.

Procedure:

1. A size 16 ring was placed under the instrument's funnel and 50 g of test powder added onto the top.
2. The instrument's trap was released allowing the powder to flow from the funnel through the ring into a collection vessel.
3. The process was repeated with the same powder until a ring with the smallest diameter was found through which the powder flowed three times out of three, without hanging up on the ring.
4. Steps (1)–(4) were repeated for all the powders.

5. Steps (1)–(4) were repeated for all the powders with carbonyl iron adsorbed onto them.

The results of the above procedure are contained in Table 5.

TABLE 5

| No. | Name of powder | Flowability Index (without carbonyl Iron) | Flowability Index (with carbonyl Iron) |
|---|---|---|---|
| 1 | Karion ® | 9 | 9 |
| 2 | Karion ® FG | 9 | 9 |
| 3 | Neosorb ® 30/60 | 6 | 10 |
| 4 | Avicel ® PH-101 | 16 | 16 |
| 5 | Emcocel ® 50-M | 14 | 14 |
| 6 | NuTab ® | 7 | 9 |
| 7 | Lactose N.F. | 16 | 18 |
| 8 | Starch 1500 | 9 | 22 |
| 9 | Starch 1500 LM | 18 | 22 |

Conclusions:

1. NuTab® had the best flowability properties.
2. The sorbitol excipients exhibited good flow properties with and without adsorbed carbonyl iron.
3. The microcrystalline cellulose excipients and lactose exhibited fair flow properties.
4. The starch excipients exhibited poor flow properties especially with carbonyl iron adsorbed to them.

COMPRESSIBILITY STUDY:

Since all of the excipients were of a directly compressible grade, they were excepted to have good compressibility. However, based upon the results from the previous studies, Nesorb®, Karion®, Emcocel® and Avicel® were the final excipients chosen for further testing. The remaining excipients were considered unacceptable to be formulated with carbonyl iron by the direct compression method. The tablets tested were compressed on a Manesty Instrumented Tablet Press. Hardness of the tablets was determined by KEY hardness tester.

Procedure:

1. 2 kilograms (kg) of carbonyl iron were prepared with each of the four excipients according to the formula found in Table 6:

TABLE 6

| Ingredient | % w/w |
|---|---|
| Excepient | 89.17 |
| Carbonyl Iron | 8.33 |
| Crospovidone | 2.0 |
| Magnesium Stearate | 0.5 |

2. The carbonyl iron was blended with each excipient in a V-blender for 10 minutes. A blend of Crospovidone, Magnesium stearate and some more excipient was then passed through the carbonyl iron blend and blending continued for another 5 minutes.

3. The blend was compressed into tablets on the Manesty instrumented tablet press. The compression parameters were:

a. compression pressure—500, 1000, 1500 and 2000 kg b. target tablet weight—600 mg c. shape—caplet 4. The hardness of the 15 tablets containing each excipient at each compression pressure was determined by the KEY hardness tester.

Results:

The hardness of the tablets in S.C.U. is shown in Table 7:

TABLE 7

| No. | Excepient used | Force 500 kg | Force 1000 kg | Force 1250 kg | Force 1500 kg | Force 2000 kg |
|---|---|---|---|---|---|---|
| 1 | Avicel ® | 14.65 | 24.51 | 28.40 | — | 43.10 |
| 2 | Emcocel ® | 7.70 | 27.0 | — | 35.80 | 44.10 |
| 3 | Neosorb ® | 2.55 | 12.21 | — | 12.58 | 26.51 |
| 4 | Karion ® | 3.90 | 14.20 | — | 25.70 | 29.80 |

1. Avicel® and Emocel® show similar compressibility profiles at compression pressures higher than 500 kg.

2. Karion® shows a superior compressibility profile than Neosorb®.

Based upon the foregoing test results, Emocel® and Karion® (having superior adsorption and compression properties) were selected for formulation development.

FORMULATION DEVELOPMENT:

2 kg blends of Emocel® and Karion®, each with carbonyl iron, were prepared for compression in composition amounts as shown in Table 8.

TABLE 8

| Ingredients | Formula I (% w/w) | Formula II (% w/w) |
|---|---|---|
| Karion | 44.585 | 12.5 |
| Emcocel | 44.585 | 78.66 |
| Carbonyl iron | 8.33 | 8.33 |
| Crospovidone | 2.00 | — |
| Mag. Stearate | 0.50 | 0.50 |

1. Karion® was mixed with carbonyl iron in a V-blender for 5 minutes. Emcocel® was added and then blending was continued for 5 additional minutes.

2. A blend of Magnesium stearate with Crospovidone and Emcocel® or just Emcocel® sieved through 30# was added and blending continued for another 5 minutes.

3. Caplets were compressed at compression pressures of 500, 1000, 1500, and 2000 kg (?) on a Manesty instrumented tablet press with the same compression parameters as used in the compression studies discussed previously.

4. Hardness (average) of 15 caplets was determined with KEY hardness tester.

5. Caplets were checked for weight uniformity.

Results:

The results of the Formulation Development compression studies can be found in Table 9. Based upon the results it appeared that formulation No. 2 compressed better than formulation No. 1.

TABLE 9

| No. | Caplets with excepients | | Force 500 kg | Force 1000 kg | Force 1500 kg | Force 2000 kg |
|---|---|---|---|---|---|---|
| 1 | Karion Emcocel | (44.585%) + (44.585%) | — | 11.7 | 21.5 | 24.8 |
| 2 | Karion Emcocel | (12.5%) + (78.66%) | 3.7 | 17.4 | 29.1 | 43.2 |

DISINTEGRATION STUDY:

Using deionized water at 37° C. in a Erweka automated disintegration apparatus, disintegration testing was performed on all caplets which contained Karion® and Emocel® and which were compressed at 2000 kg. Since all the caplets have disintegration times (See Table 10) within 10 minutes, no optimization was necessary.

TABLE 10

| No. | Composition of Caplets Carbonyl Iron 8.33% + | | Disintegration Time (mm:ss) | % RSD |
|---|---|---|---|---|
| 1 | Karion ® | (89.17%) | 4:08 | 4.8 |
| 2 | Neosorb ® | (89.17%) | 3:54 | 11.5 |
| 3 | Emcocel ® | (89.17%) | 1:39 | 23.2 |
| 4 | Avicel ® | (89.17%) | 00:24 | 30.8 |
| 5 | Emcocel ® Karion ® | (44.585%) + (44.585%) | 7:33 | 18.6 |
| 6 | Emcocel ® Karion ® | (78.66%) + (12.5%) | 3:17 | 15.4 |

DISSOLUTION STUDY:

Dissolution studies were performed on pure carbonyl iron, carbonyl iron caplets and marketed preparations such as Feosol™ tablets, Feosol™ capsules and Slow-Fe™ Tablets. A Hanssen dissolution apparatus with a VanderKamp automated sampler was used.

Procedure:
1. Dissolution:
   a. The dissolution procedure was set up with the following parameters:
      dissolution medium—0.1 N HCl
      temperature—37° C.
      medium quantity—900 ml
      type—USP spindle
      rotation speed—100 rpm
      sample volume—5 ml
      sampling protocol—5 min, 15 min, 30 min, 45 min, 60 min, 120 min, 180 min and 240 min.
   b. The samples were diluted and analysed by a Varian Atomic Absorption Spectrometer against known standards.
2. Content Analysis: (duplicate)
   a. 20 tablets were crushed to form a composite from which the equivalent of one tablet was accurately weighed.
   b. Each sample tablet was digested with HCl and the appropriate dilutions were performed.
   c. The samples were analysed by a Varian Atomic Absorption Spectrometer against known standards.

Results:
1. Carbonyl iron powder by itself was slow to dissolve.
2. Carbonyl iron caplets made with soluble excepients i.e., Karion® gave a better iron recovery than with insoluble excepients like Emcocel®.
3. With an increase in the percentage of Emcocel® in the formulation, the recovery of iron decreases in a given period.
4. Lactose plus Karion® caplets show an 80% iron recovery.

Conclusions:
1. Soluble excipients provide a better recovery of iron as compared to insoluble excipients.
2. These data suggest that a slow releasing iron caplet could be formulated according to this invention by varying the ratio of soluble/water insoluble or soluble/soluble excipients.

The carbonyl iron tablet according to this invention may be made by first preparing a premix consisting of the optional disintegrant and lubricant and a portion of the filler (lactose). In a separate vessel, the sorbitol and carbonyl iron are blended for approximately 5 minutes, followed by adding the remainder of the filler. This carbonyl iron mixture is then added to the premix in order to form a final blend. Flavors and other standard tablet excipients may be added at this time. The final blend is then compressed into tablets by the direct compression technique. The tablets may be coated with standard film coats in order to give the tablets a colored or clear appearance.

According to this invention a tablet may be formulated with specific ingredient amounts as follows:

| Item | Name | mg/caplet (coated) | % w/w (coated) |
|---|---|---|---|
| 1 | Magnesium Stearate, NF (#2255) | 3.000 | 0.4819 |
| 2 | Stearic Acid, NF (Triple Pressed) | 3.000 | 0.4819 |
| 3 | Polyethylene Glycol 8000, NF (Powder) | 3.000 | 0.4819 |
| 4 | Crospovidone, NF (Polyplasdone XL) | 6.000 | 0.9638 |
| 5 | Lactose, NF Anhydrous | 267.000 | 42.8916 |
| 6 | Sorbitol, NF | 267.000 | 42.8916 |
| 7 | Carbonyl Iron, FCC (Ferronyl Iron) | 51.000 | 8.1928 |
| 8 | Purified Water, USP | 0.000 | 0.000 |
| 9 | Opadry II YS-22-15039 Red** | 21.000 | 3.3735 |
| 10 | Opadry II Y-19-7483 Clear*** | 1.500 | 0.2410 |
|  | TOTAL | 622.500 | 100.000 |

** Opadry II YS-22-15039 Red contains:
Hydroxypropyl Methylcellulose
Polydextrose
FD&C Red #40 Aluminum Lake
Titanium Dioxide
Polyethylene Glycol
FD&C Yellow #6 Aluminum Lake
FD&C Blue #2 Aluminum Lake
***Opadry III Y-19-7483 Clear contains:
Hydroxypropyl Methylcellulose
Maltodextrin
Polyethylene Glycol

What is claimed is:

1. A pharmaceutical composition for direct compression tableting comprising about 8.0–9.0 percent weight/weight of the total composition of carbonyl iron as an active ingredient and sorbitol as a suitable carrier.

* * * * *